(12) United States Patent
Ofek et al.

(10) Patent No.: US 11,872,367 B2
(45) Date of Patent: Jan. 16, 2024

(54) ANTIMICROBIAL AND ANTITHROMBOGENIC GASEOUS RELEASE DEVICE AND RELATED SYSTEMS AND METHODS

(71) Applicant: Becton, Dickinson and Company, Franklin Lakes, NJ (US)

(72) Inventors: Gidon Ofek, Millcreek, UT (US); Christopher Quach, Salt Lake City, UT (US); James Freasier, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 265 days.

(21) Appl. No.: 17/128,868

(22) Filed: Dec. 21, 2020

(65) Prior Publication Data

US 2021/0205530 A1    Jul. 8, 2021

Related U.S. Application Data

(60) Provisional application No. 62/956,546, filed on Jan. 2, 2020.

(51) Int. Cl.
*A61M 39/16*    (2006.01)
*A61M 5/14*    (2006.01)
(Continued)

(52) U.S. Cl.
CPC .......... *A61M 5/14* (2013.01); *A61M 25/0026* (2013.01); *A61M 25/02* (2013.01); *A61M 39/0247* (2013.01); *A61M 39/10* (2013.01); *A61M 2025/0266* (2013.01); *A61M 2039/0258* (2013.01); *A61M 2202/0275* (2013.01); *A61M 2205/0205* (2013.01); *A61M 2205/7536* (2013.01)

(58) Field of Classification Search
CPC .. A61M 2025/0019; A61M 2025/0056; A61M 2039/0258; A61M 2202/0275; A61M 2205/0205; A61M 2205/7536; A61M 39/162
See application file for complete search history.

(56) References Cited

U.S. PATENT DOCUMENTS 5,354,264 A    10/1994 Bae et al.
2003/0064028 A1*    4/2003 Fine ........................ A61K 33/34
424/43
(Continued)

*Primary Examiner* — Deanna K Hall
(74) *Attorney, Agent, or Firm* — Kirton McConkie; Whitney Blair; Kevin Stinger

(57) ABSTRACT

A system for infusing a gas into a vascular access device may include a catheter interface, which may include a distal end, a proximal end, and a lumen extending between the distal end and the proximal end. The system may also include a connector disposed on an outer surface of the catheter interface. The connector may be configured to couple to a reservoir. The reservoir may include a housing, which may include an opening and an impermeable wall. The opening may be configured to couple to the connector of the catheter interface. The reservoir may also include a molecular precursor to a gaseous agent that is suspended in a hydrogel and disposed within the housing. The gaseous agent may be antimicrobial, antithrombogenic, or both antimicrobial and antithrombogenic.

8 Claims, 9 Drawing Sheets

(51) Int. Cl.
*A61M 25/00* (2006.01)
*A61M 25/02* (2006.01)
*A61M 39/10* (2006.01)
*A61M 39/02* (2006.01)

(56) References Cited

U.S. PATENT DOCUMENTS

| | | |
|---|---|---|
| 2013/0261537 A1 | 10/2013 | Hofler et al. |
| 2015/0202422 A1* | 7/2015 | Ma ............... A61M 39/0693 604/167.02 |
| 2015/0231384 A1 | 8/2015 | Ma et al. |
| 2019/0234540 A1 | 8/2019 | Marici et al. |
| 2020/0197686 A1* | 6/2020 | Anderson ............ A61M 39/18 |

* cited by examiner

ANTIMICROBIAL AND ANTITHROMBOGENIC GASEOUS RELEASE DEVICE AND RELATED SYSTEMS AND METHODS

RELATED APPLICATIONS

This application claims the benefit of U.S. Provisional Application No. 62/956,546, filed Jan. 2, 2020, and entitled ANTIMICROBIAL AND ANTITHROMBOGENIC GASEOUS RELEASE DEVICE AND RELATED SYSTEMS AND METHODS, which is incorporated herein in its entirety.

BACKGROUND

Catheter-related blood-stream infections (CRBSIs) may be a common complication when using vascular access devices. Vascular access device infection resulting in CRBSIs may be caused by failure to regularly clean the device, a non-sterile insertion technique, or by pathogens entering the fluid flow path through either end of the path subsequent to insertion of the vascular access device. Studies have shown the risk of CRBSI increases with catheter indwelling periods. When a vascular access device becomes contaminated, pathogens adhere to the vascular access device, colonize and form a biofilm. The biofilm is resistant to most biocidal agents and provides a replenishing source for pathogens to enter a patient's bloodstream and cause an infection.

Antimicrobial or antithrombogenic agents have been incorporated into coatings applied to surfaces of vascular access devices. These coatings may be difficult or expensive to apply to the device. Another issue with coatings is that they increase the manufacturing costs of the vascular access devices, requiring a relatively long period of time for either solvents to evaporate or coatings to harden. Further, antimicrobial or antithrombogenic activity of the coating diminish over the indwelling period, lowering the effectiveness of the antimicrobial or antithrombogenic agent. Accordingly, there is a need in the art for improved means for providing antimicrobial and antithrombogenic capability to medical devices of various types, and particularly to devices related to infusion therapy.

The subject matter disclosed and claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a reservoir for housing a molecular precursor to a gaseous agent suspended in a hydrogel disposed within the housing, in which the gaseous agent is antimicrobial or antithrombogenic, as well as related systems and methods. In some embodiments, a reservoir may include a housing having an opening and a gas impermeable wall. The opening may be configured to couple to a vascular access device. In some embodiments, the reservoir may also include a molecular precursor to a gaseous agent that may be suspended in a hydrogel and disposed within the housing. In some embodiments, the gaseous agent may be antimicrobial, antithrombogenic, or both antimicrobial and antithrombogenic.

In some embodiments, the opening of the housing may also include a membrane. In some embodiments, the membrane may be gas-permeable and hydrophobic. In some embodiments, the housing may also include a removable or pierceable seal that covers the opening. In some embodiments, the molecular precursor to the gaseous agent may be S-nitroso-N-acetylpenicillamine, S-nitrosoglutathione, sodium nitroprusside, or a combination thereof. In some embodiments, the gaseous agent may be nitric oxide.

In some embodiments, the housing of the reservoir may include a gas permeable partition that separates the housing into a first chamber and a second chamber. In some embodiments, the first chamber may include the molecular precursor to the gaseous agent suspended in the hydrogel and the second chamber may include a catalyst for the molecular precursor to release the gaseous agent. In some embodiments, the second chamber may include a catalyst within the housing. In some embodiments, the catalyst may be water or saline. In some embodiments, the catalyst may further include a metallic catalyst. In some embodiments, the second chamber may be separated from the hydrogel by a pierceable water impermeable membrane.

In some embodiments, the reservoir housing may include an upper housing and a lower housing. In some embodiments, the upper housing and the lower housing may both include a gas impermeable wall. In some embodiments, the lower housing may further include the opening and the upper housing may be configured to couple to the lower housing.

In some embodiments, the housing may also include a piercing mechanism that pierces the water impermeable membrane upon coupling the reservoir to the vascular access device to catalyze the production of the gaseous agent from the molecular precursor. In some embodiments, the reservoir may include a wick that penetrates the housing.

In some embodiments, a system for infusing a gas into a vascular access device may include a catheter interface. In some embodiments, the catheter interface may include a distal end, a proximal end, and one or more lumens extending between the distal end and the proximal end. In some embodiments, the catheter interface may include a connector disposed on an outer surface of the catheter interface. In some embodiments, the connector may be configured to couple to a reservoir and allow passage of a gaseous agent from the reservoir to the one or more lumens. In some embodiments, the reservoir includes a housing and a molecular precursor to a gaseous agent suspended in a hydrogel disposed within the housing. In some embodiments, the gaseous agent may permeate through the connector and into the one or more lumens. In some embodiments, the gaseous agent may provide antimicrobial or antithrombogenic protection, or both antimicrobial and antithrombogenic protection to surfaces of the catheter system.

In some embodiments, the system for infusing a gas into a vascular access device may include a fluid pathway in fluid communication between the reservoir and the one or more lumens. In some embodiments, the connector may be a luer connector or a molded junction fitting. In some embodiments, the reservoir housing may mechanically couple to the catheter adapter in an interference fit. In some embodiments, the connector may also include a recessed projection mechanism. In some embodiments, the opening of the housing may include a seal and upon coupling the connector to the reservoir the recessed projection may pierce the seal. In some embodiments, the connector may include a gas-permeable and hydrophobic membrane.

In some embodiments, a system for infusing a gas into a vascular access device may include a stabilization device configured to couple to the vascular access device and a reservoir. In some embodiments, the reservoir may include a housing and a molecular precursor to a gaseous agent suspended in a hydrogel disposed within the housing. In some embodiments, the stabilization device may also include an adhesive pad such that the stabilization device anchors the vascular access device to an insertion site. In some embodiments, the vascular access device may include a connector disposed on an outer surface. In some embodiments, the connector may be a molded junction fitting such that the opening of the housing couples to the catheter system in an interference fit.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
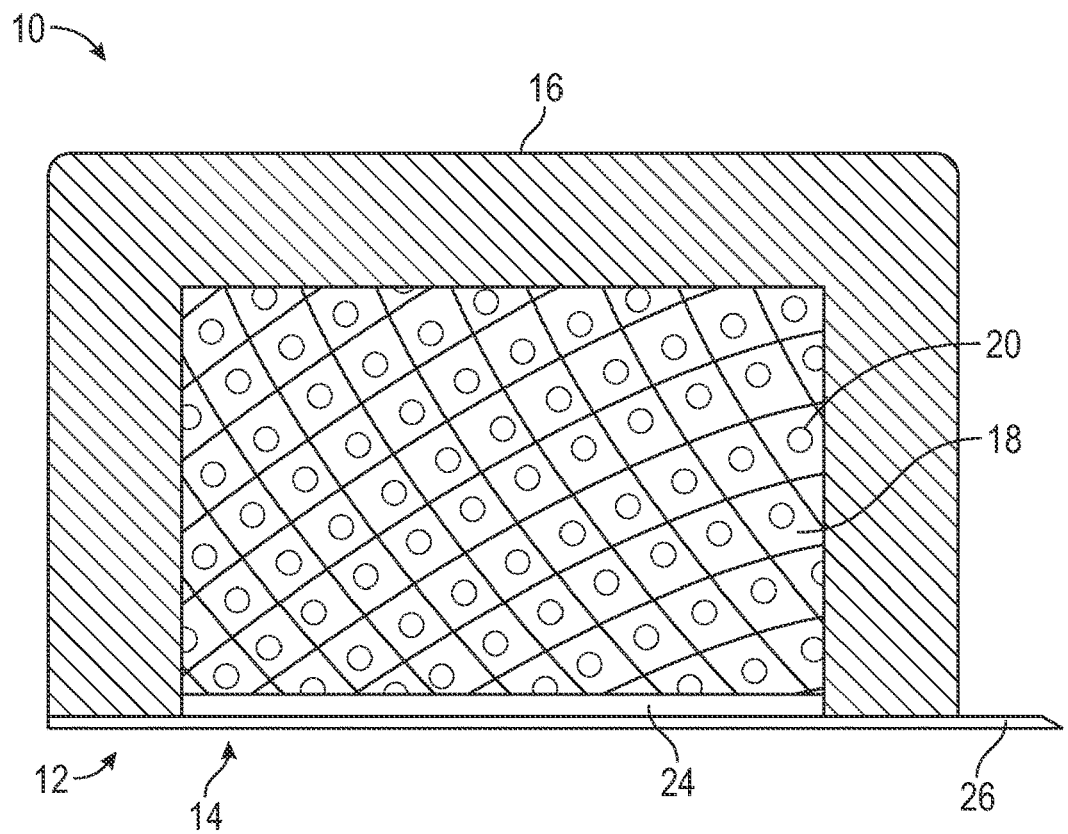
FIG. 1A is a cross-sectional view of an example reservoir, according to some embodiments.
Figure 1B:
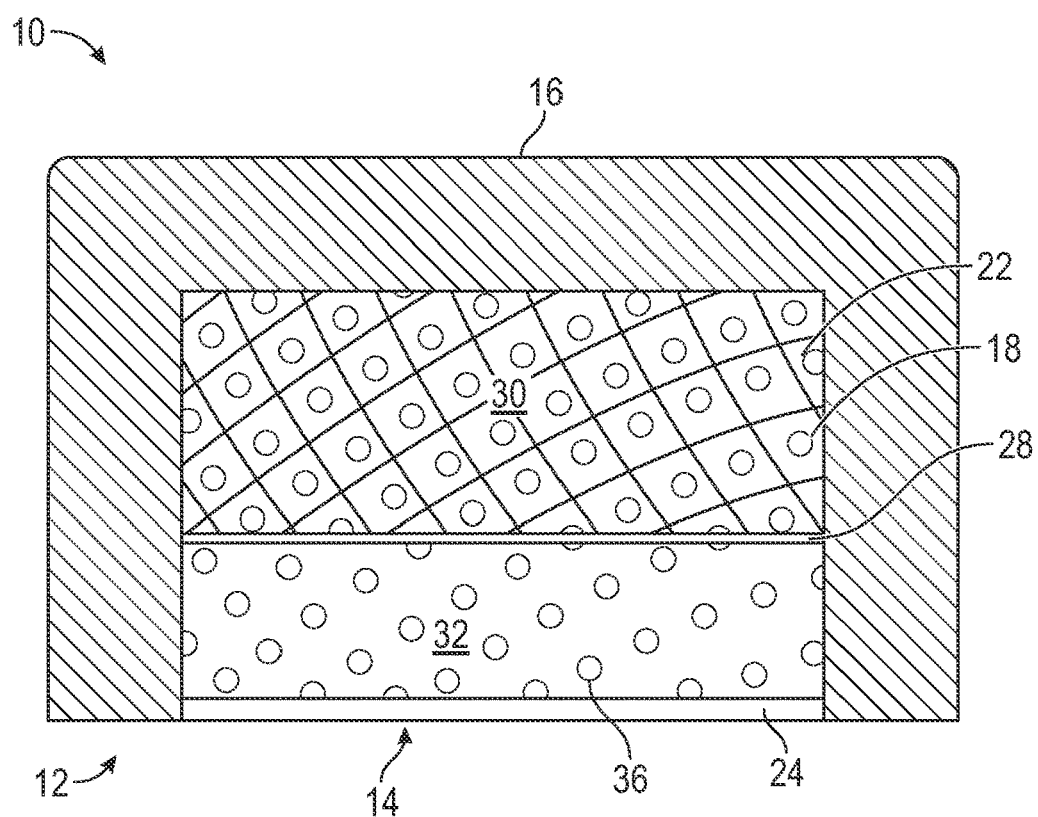
FIG. 1B is a cross-sectional view of another example reservoir, according to some embodiments.

Referring now to FIGS. 1A-1B, in some embodiments, a reservoir 10 may include a housing 12, which may include an opening 14 and a gas impermeable wall 16. In some embodiments, the opening 14 may be configured to couple to a vascular access device. In some embodiments, the reservoir 10 may include a molecular precursor 18 to a gaseous agent 20 suspended in a hydrogel 22. In some embodiments, the hydrogel 22 may be disposed within the housing 12. In some embodiments, the gaseous agent 20 may be antimicrobial, antithrombogenic, or antimicrobial and antithrombogenic.

In some embodiments, the opening 14 may include a membrane 24. In some embodiments, the membrane 24 may retain the hydrogel 22 within the housing 12. In some embodiments, the membrane 24 may be hydrophobic. In some embodiments, the membrane 24 may be gas permeable. In some embodiments, the gaseous agent 20 may pass through the membrane 24 and the hydrogel 22 is retained within the housing 12. In some embodiments, the membrane 24 may be constructed of a silicone. In some embodiments, the membrane 24 may be a polyester co-polymer. In other embodiments, the membrane 24 may be a fluorinated polymer. In other embodiments, the membrane 24 may be constructed of any suitable material known in the art that is hydrophobic and gas permeable.

In some embodiments, the gaseous agent 20 may be nitric oxide. In some embodiments, the gaseous agent 20 may be any other gas that exhibits antimicrobial and/or antithrombogenic properties. In some embodiments, the molecular precursor 18 may be S-nitroso-N-acetylpenicillamine (SNAP), S-nitrosoglutathione, sodium nitroprusside (SNP), or a combination thereof. In some embodiments, the molecular precursor 18 may be any precursor to a gaseous agent that may be suspended in a hydrogel 22 or any other type of suitable antimicrobial or antithrombogenic agent delivery system known in the art. In some embodiments, the hydrogel 22 may be polyethylene glycol (PEG). In other embodiments, the hydrogel 22 may be alginate or other suitable hydrogel.

In some embodiments, the housing 12 may be cylindrical. In some embodiments, the gas impermeable wall 16 may be impermeable to the gaseous agent 20. In some embodiments, the gas impermeable wall 16 is impermeable to the molecular precursor 18 and the hydrogel 22. In some embodiments, the gas impermeable wall 16 may be constructed of a high durometer urethane. In some embodiments, the gas impermeable wall 16 may be a polyester, high density polyethylene, polypropylene, polystyrene, or any suitable plastic or material known in the art. In some embodiments, the gas impermeable wall 16 may be spherical shaped, cubic shaped, or other geometric shape.

In some embodiments, the membrane 24 may mechanically couple to an interior wall of the gas impermeable wall 16. In some embodiments, the membrane 24 may be coupled to the gas impermeable wall with an adhesive. In some embodiments, the housing 12 may further include a seal 26 that covers the opening 14. In some embodiments, the seal 26 may protect the membrane from puncture or exposure. In some embodiments, the seal 26 may be removable and/or pierceable. In some embodiments, the seal 26 may be impermeable to gas or fluids of any type. In some embodiments, the seal 26 may be a foil, plastic, or any suitable seal known in the art. In some embodiments, the seal 26 may be coupled to the housing 12 with an adhesive or any other suitable attachment method.

In some embodiments, the reservoir 10 may also include a partition 28 that may be gas permeable. In some embodiments, the partition 28 may separate the housing 12 into a first chamber 30 and a second chamber 32. In some embodiments, the first chamber 30 may include the molecular precursor 18 suspended in the hydrogel 22, and the second chamber 32 may include a catalyst for the molecular precursor 18. In some embodiments, the partition 28 may separate the housing 12 such that the first chamber 30 and the second chamber 32 are about the same size. In some embodiments, the second chamber 32 may be proximate to the opening 14. In some embodiments, the partition 28 may separate the housing 12 such that the first chamber 30 has a bigger size than the second chamber 32. In some embodiments, the partition 28 may separate the reservoir 10 such that both the first chamber 30 and the second chamber 32 are proximate to the opening 14 and/or the membrane 24.

Referring now to FIGS. 2A-2E, in some embodiments, the second chamber 32 may be separated from the first chamber 30 by a pierceable water impermeable membrane 34. In some embodiments, the second chamber 32 may be a thin film of water or saline within the housing 12. In some embodiments, the second chamber 32 may include a water soluble catalyst 36.

In some embodiments, the catalyst 36 for the molecular precursor 18 may include pure water, deoxygenated, deionized, or ionized water. In other embodiments, the catalyst 36 may include an aqueous buffer solution. In some embodiments, the catalyst 36 may be metallic. In some embodiments, the catalyst 36 may include an aqueous solution with catalyst ions or elements therein. In some embodiments, the catalyst 36 may be ions or elements that may include copper, iron, zinc, selenium or a combination thereof. In some embodiments, the aqueous buffer solution may be any suitable solution known in the art.

In some embodiments, water or an aqueous solution may initiate the release of nitric oxide from the molecular precursor 18. In some embodiments, SNAP, SNP, S-nitrosoglutathione and other nitrosating agents may undergo a spontaneous denitrosation or nitric oxide donation in an aqueous solution. In some embodiments, SNP may be readily soluble in water and/or buffer solutions and releases nitric oxide in the presence of water. In some embodiments, the reservoir 10 may continuously release the gaseous agent 20.

In some embodiments, the housing 12 may include a piercing mechanism 38. In some embodiments, the piercing mechanism 38 may be configured to pierce the pierceable water impermeable membrane 34. In some embodiments, upon piercing the pierceable water impermeable membrane 34, the molecular precursor 18 may be wetted and the gaseous agent 20 may be released from the hydrogel 22. In some embodiments, the piercing mechanism 38 may pierce the water impermeable membrane 34 upon coupling the reservoir 10 to a vascular access device.

In some embodiments, the piercing mechanism 38 may include a pointed end 40. In some embodiments, upon contact between the pointed end 40 and the pierceable water impermeable membrane 34, water and/or buffer solution may pass through the pierceable water impermeable membrane 34 to hydrate the hydrogel 22. In some embodiments, the piercing mechanism 38 may be coupled to the housing 12. In some embodiments, the piercing mechanism 38 may extend to or beyond an outer surface of the housing 12. In some embodiments, the piercing mechanism 38 may extend through the membrane 24. In some embodiments, the piercing mechanism 38 may extend outside the impermeable gas wall 16. In some embodiments, by pushing a portion of the piercing mechanism 38 that extends to or beyond the outer surface of the housing 12, the pointed end 40 pierces the pierceable water impermeable membrane 34. In some embodiments, the piercing mechanism 38 may be pushed by coupling the reservoir 10 to a vascular access device. In some embodiments, the piercing mechanism 38 may be pressed by a user, such as a clinician.

Figure 2A:
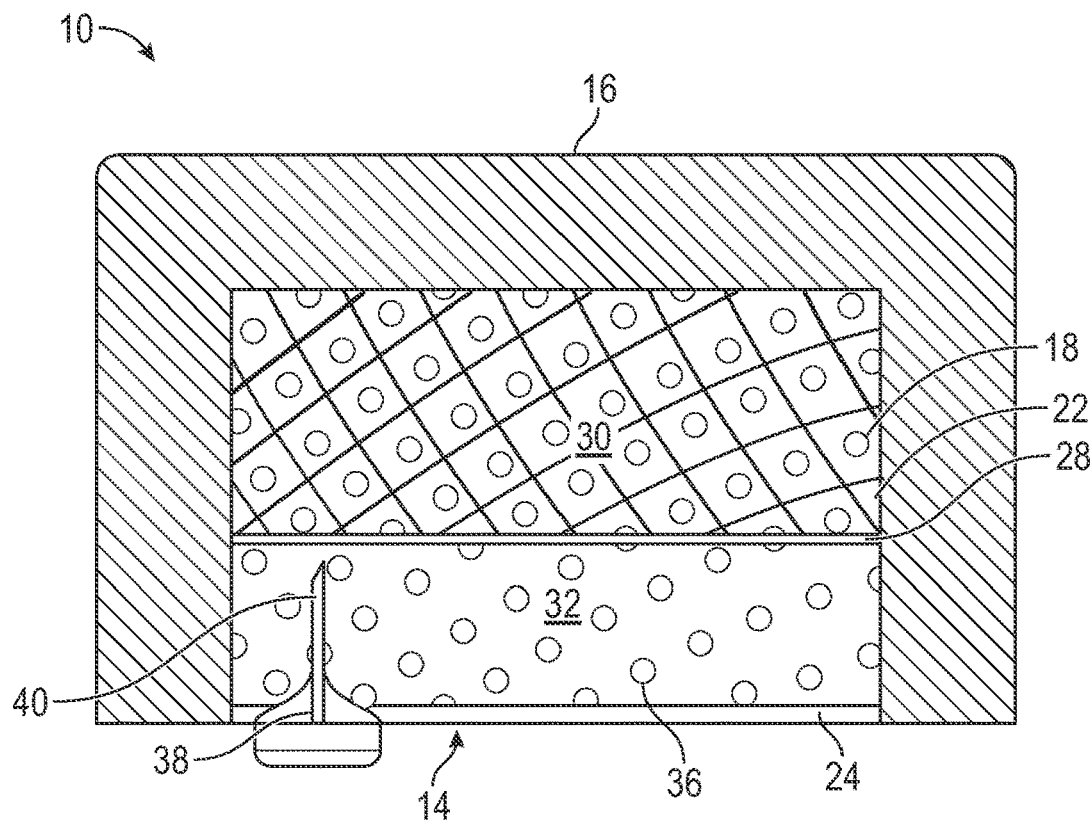
FIG. 2A is a cross-sectional view of another example reservoir, according to some embodiments.
Figure 2B:
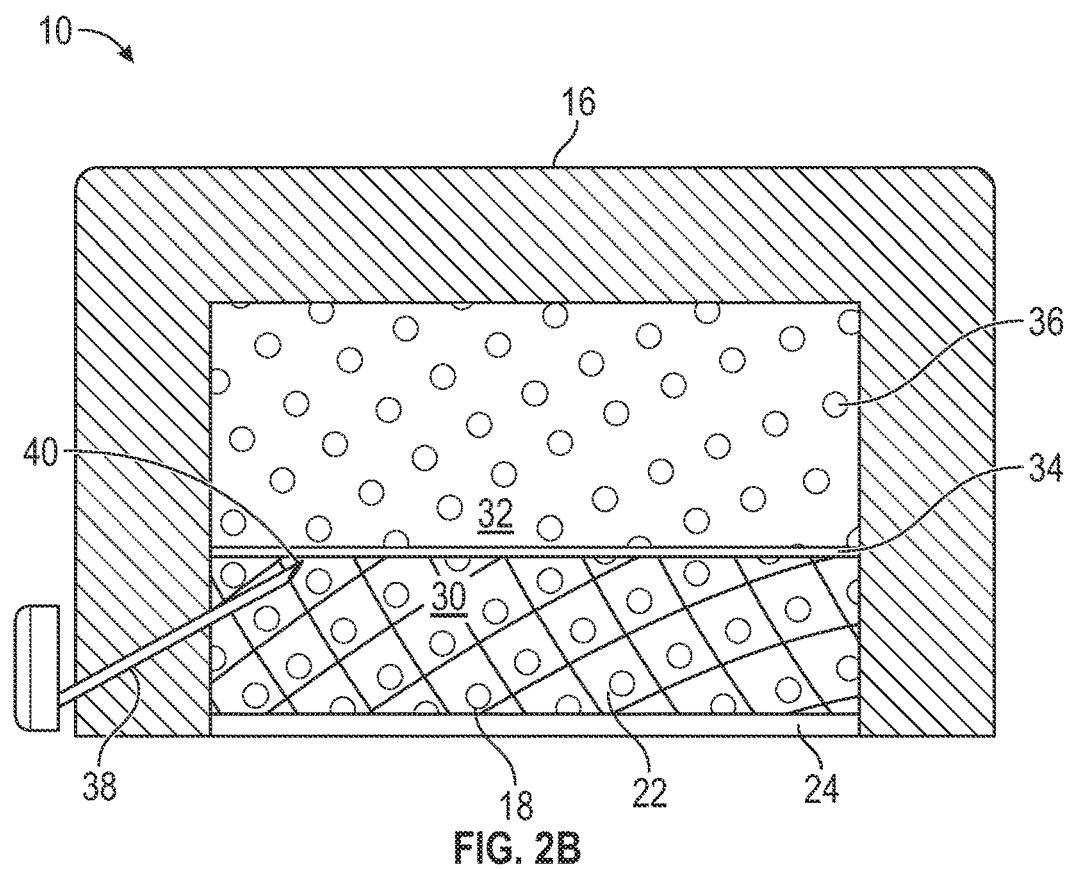
FIG. 2B is a cross-sectional view of another example reservoir, according to some embodiments.
Figure 2C:
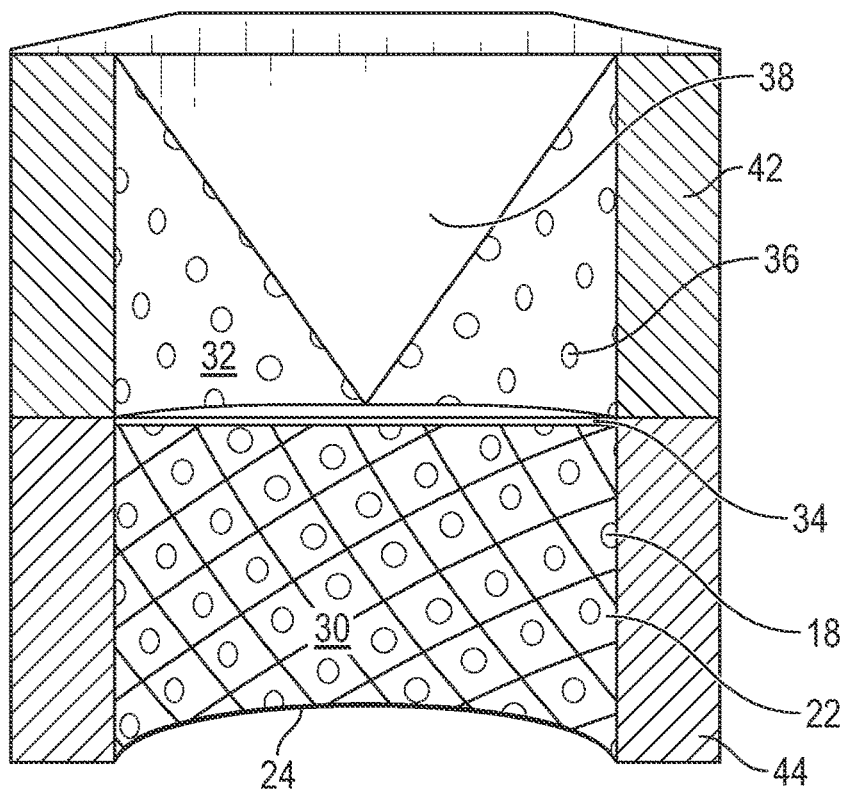
FIG. 2C is a cross-sectional view of another example reservoir, according to some embodiments.
Figure 2D:
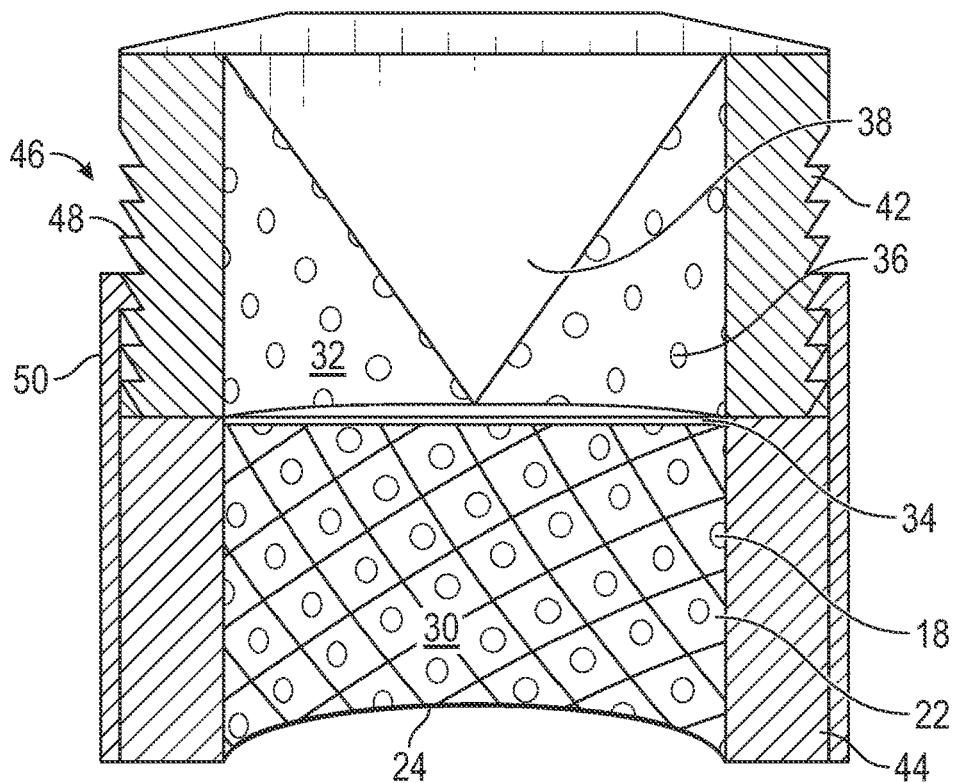
FIG. 2D is a cross-sectional view of another example reservoir, according to some embodiments.
Figure 2E:
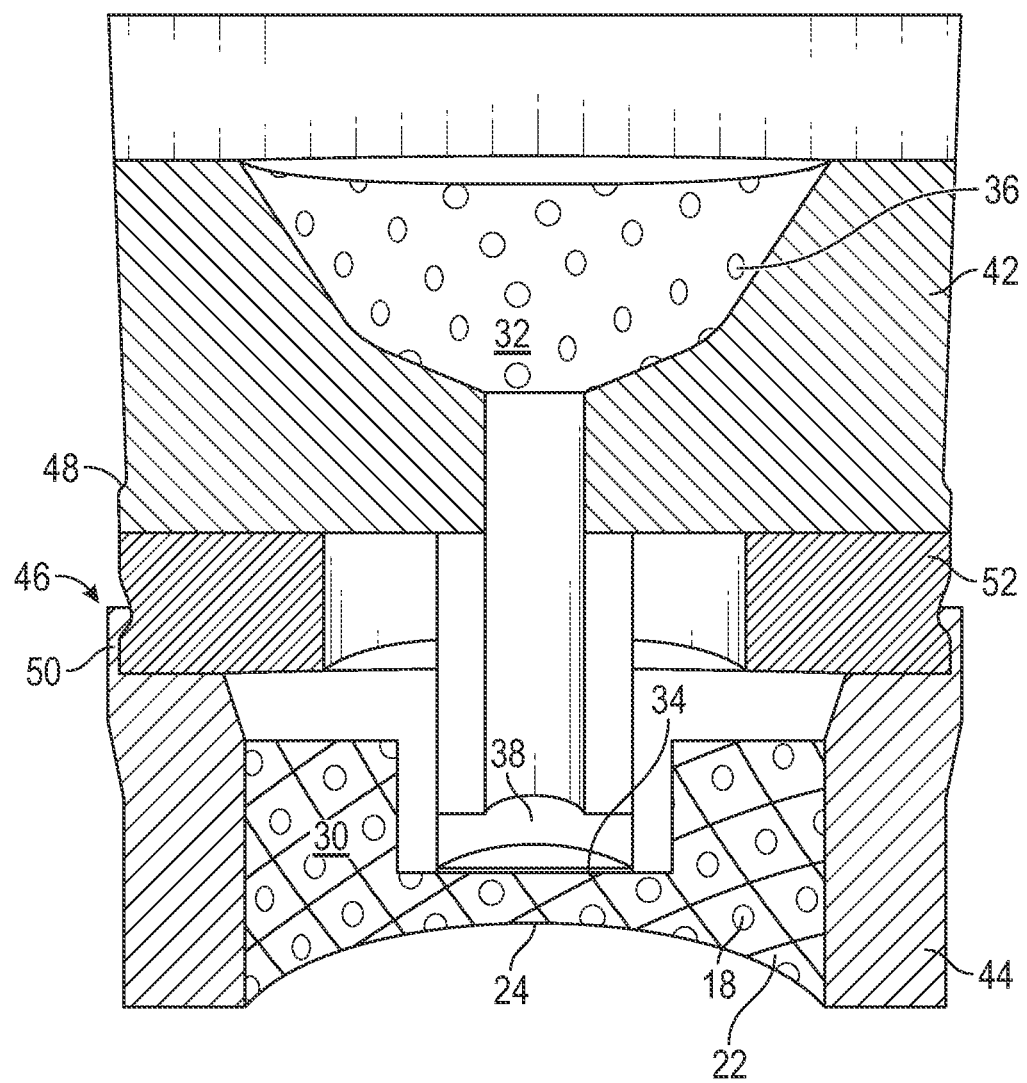
FIG. 2E is a cross-sectional view of another example reservoir, according to some embodiments.

Referring to FIGS. 2C-2E, in some embodiments, the housing 12 may include two separable portions, an upper housing 42 and a lower housing 44. In some embodiments, the upper housing 42 and the lower housing 44 may include the impermeable gas wall 16. In some embodiments, the lower housing 44 may include the opening 14. In some embodiments, the upper housing 42 may be configured to couple to the lower housing 44.

In some embodiments, the upper housing 42 may include the first chamber 30. In other embodiments, the upper housing 42 may include the second chamber 32. In some embodiments, the upper housing 42 may include both the first chamber 30 and the second chamber 32. In some embodiments, the upper housing 42 may include the piercing mechanism 38.

In some embodiments, the lower housing 44 may include the first chamber 30. In other embodiments, the lower housing 44 may include the second chamber 32. In some embodiments, the lower housing 44 may include both the first chamber 30 and the second chamber 32. In some embodiments, the lower housing 44 may include the piercing mechanism 38. In some embodiments, the piercing mechanism 38 may be a conical shape. In some embodiments, the piercing mechanism 38 may be integrated into the upper housing 42 or the lower housing 44 and may pierce the water impermeable membrane 34 upon coupling the reservoir 10 to a vascular access device.

In some embodiments, upper housing 42 and the lower housing 44 may be constructed of the same material. In some embodiments, both the upper housing 42 and the lower housing 44 may be constructed of a urethane having a high durometer. In some embodiments, the high durometer urethane may prevent the gaseous agent 20 from diffusing or flowing out of the impermeable gas wall 16. In some embodiments, upper housing 42 may be constructed of a material having a greater durometer than the lower housing 44. In other embodiments, the lower housing 44 may have a greater durometer than the upper housing 42.

In some embodiments, the upper housing 42 and the lower housing 44 may be the same size. In some embodiments the upper housing 42 and the lower housing 44 may be the same volume and/or length. In some embodiments, the size of the upper housing 42 or lower housing 44 may be different. In some embodiments, the first chamber 30 that includes the molecular precursor 18 suspended in the hydrogel 22, may have a greater length than the second chamber 32 that includes the catalyst for the molecular precursor 18. In some embodiments, the greater length of the first chamber 30 may prevent the piercing mechanism 38 from inadvertently piercing the membrane 24.

In some embodiments, the upper housing 42 and the lower housing 44 may couple together with a clipping mechanism 46. In some embodiments, the clipping mechanism 46 may include teeth 48 and a clip 50 that couple together and keep the upper housing 42 coupled to the lower housing 44. In some embodiments, the clipping mechanism 46 may have multiple teeth 48 such that the upper housing 42 and lower housing 44 may ratchet together such that the piercing mechanism 38 pierces the water impermeable membrane 34 when the upper housing 42 and the lower housing 44 are pushed together.

In some embodiments, the reservoir 10 may include a safety mechanism 52 that may prevent the piercing mechanism 38 from inadvertently piercing the water impermeable membrane 34. In some embodiments, the safety mechanism 52 may be a cylindrical spacer between the upper housing 42 and the lower housing 44. In some embodiments the safety mechanism 52 may be removable such that the safety mechanism 52 may be removed and discarded prior to coupling the reservoir 10 to a vascular access device. In some embodiments, the safety mechanism 52 may be compressible.

Figure 2F:
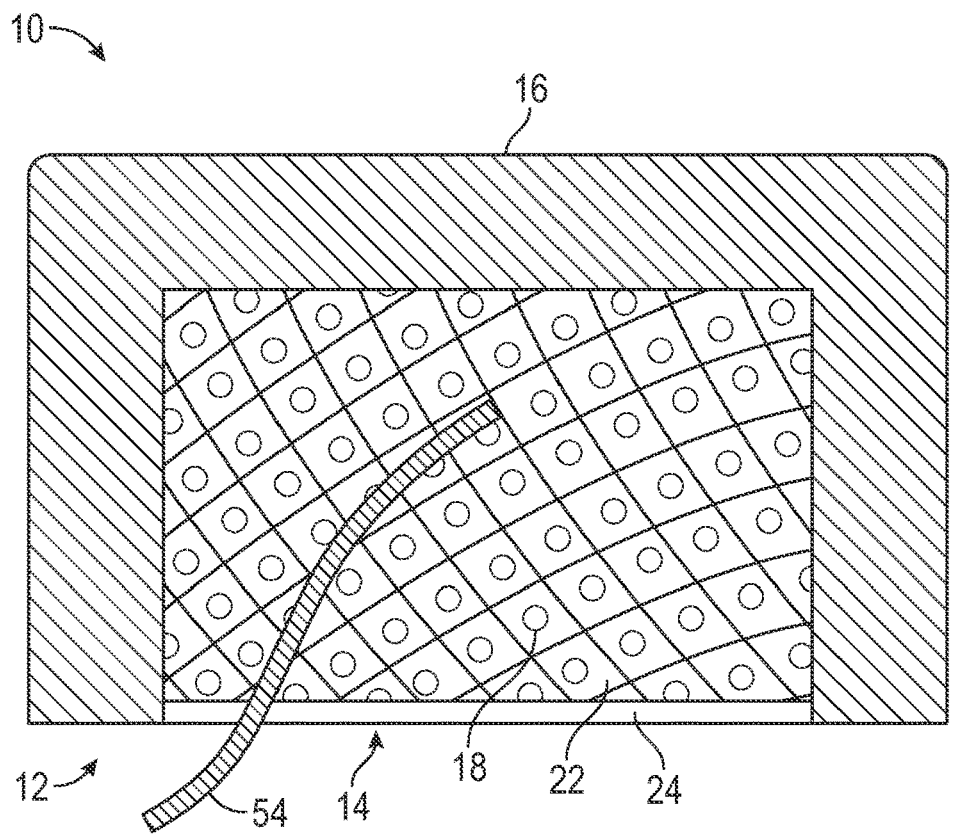
FIG. 2F is a cross-sectional view of another example reservoir, according to some embodiments.

Referring now to FIG. 2F, in some embodiments, the reservoir 10 may include a wick 54. In some embodiments, the wick 54 may be a water-transporting or solution-transporting device that enables water and/or aqueous solution to be transported into the housing 12 to wet the hydrogel 22. In some embodiments, the wick 54 may extend through the membrane 24 or through the impermeable gas wall 16. In some embodiments, the wick 54 may be configured to be wetted upon coupling the reservoir to a vascular access device. In some embodiments, the wick 54 may be constructed of a synthetic fiber. In some embodiments, the wick 54 may be constructed of polyester. In other embodiments, the wick 54 may be constructed of cotton, other natural fibers, or any other suitable wicking material.

Figure 3A:
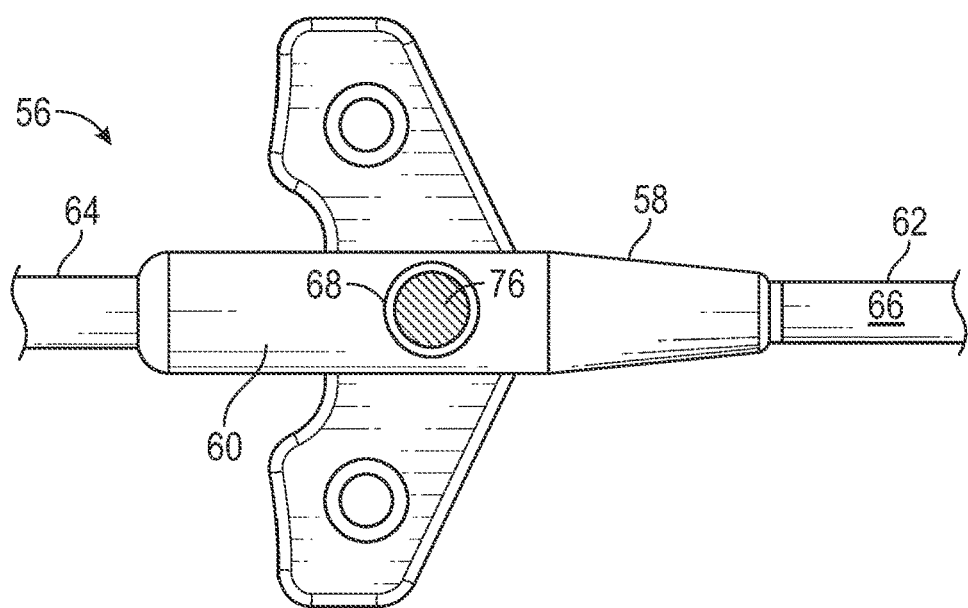
FIG. 3A is a top view of a vascular access device, according to some embodiments.
Figure 3B:
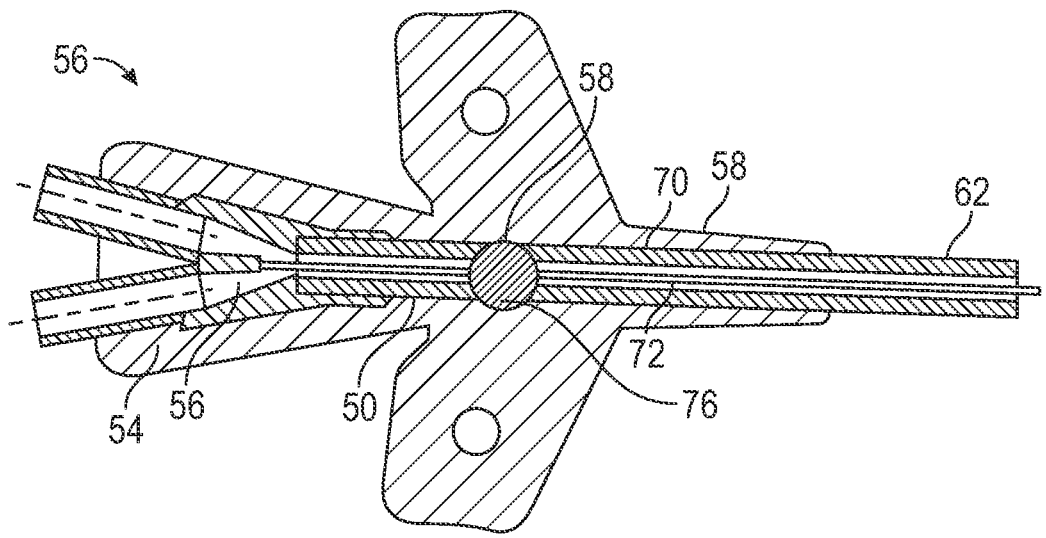
FIG. 3B is a cross-sectional view of the vascular access device of FIG. 4A, according to some embodiments.

Referring now to FIGS. 3A-3B, in some embodiments, a system 56 for infusing a gas into a vascular access device 58 may include a catheter interface 60. In some embodiments, the catheter interface 60 may include a distal end 62, a proximal end 64, and one or more lumens 66 extending between the distal end 62 and the proximal end 64. In some embodiments, the catheter interface 60 may include a catheter adapter. In some embodiments, the catheter interface 60 may include any suitable vascular access device 58.

In some embodiments, the system 56 may include a connector 68 disposed on an outer surface 70 of the catheter interface 60. In some embodiments, the connector 68 may be configured to couple to the reservoir 10. In some embodiments, the gaseous agent 20 may permeate through the connector 68 and into the one or more lumens 66. The one or more lumens 66 may include at least one interior surface 72 of the catheter interface 60. In some embodiments, the gaseous agent 20 may provide antimicrobial, antithrombogenic, or antimicrobial and antithrombogenic protection to the outer surface 70 and/or the interior surface 72 of the catheter interface 60. In some embodiments, the gaseous agent 20 may provide antimicrobial and/or antithrombogenic protection to the outer surface 70 by diffusing through the catheter interface 60. In some embodiments, the reservoir 10 may be removed from the connector 68 and replaced after the molecular precursor 18 has been depleted. Thus, the reservoir 10 is renewable or replaceable as required to provide antimicrobial and/or antithrombogenic protection to the interior surfaces 72 and/or outer surfaces 70 of the catheter interface 60.

Figure 4A:
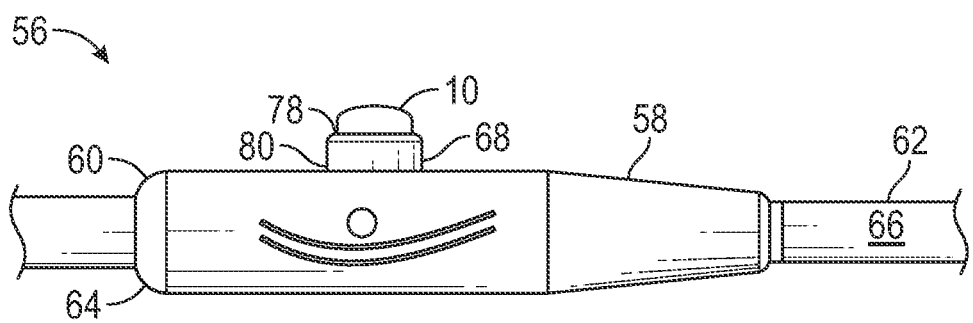
FIG. 4A is a side view of a vascular access device and a reservoir, according to some embodiments.
Figure 4B:
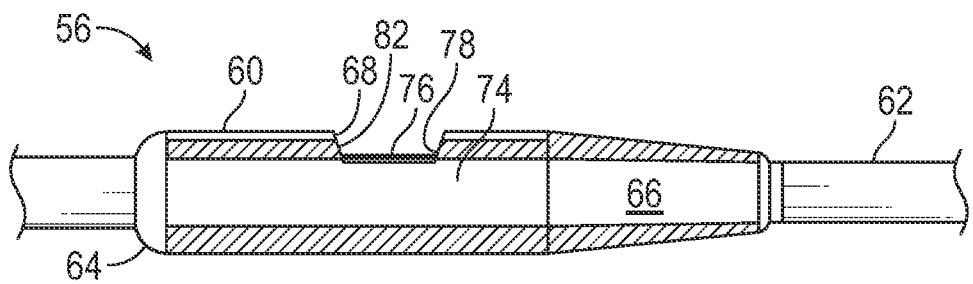
FIG. 4B is a cross-section view of the vascular access device of FIG. 5A, according to some embodiments.

Referring now to FIGS. 4A-4B, in some embodiments, the connector 68 may be located on a top portion of the catheter interface 60, opposite the portion of the catheter interface 60 that may contact a skin surface of a patient. In some embodiments, the catheter interface 60 may include a fluid pathway 74 in fluid communication between the one or more lumens 66 and the reservoir 10. In some embodiments, the fluid pathway 74 may be an open pathway for gas and/or liquid. In some embodiments, the fluid pathway 74 may be only gas-permeable. In some embodiments, the connector 68 may include a connector membrane 76. In some embodiments, the connector membrane 76 may be gas-permeable and hydrophobic. In some embodiments, the gaseous agent 20 may permeate through the outer surface 70 of the catheter interface 60.

In some embodiments, the connector 68 may include a molded junction fitting 78 that may couple to the reservoir 10 in an interference fit. In some embodiments, the molded junction fitting 78 may include an extended fitting 80 that extends from the surface of the catheter interface 60. In some embodiments, the reservoir may engage in an interference fit with an interior surface of the extended fitting 80. In other embodiments, the reservoir 10 may engage in an interference fit with an outer surface of the extended fitting 80. The extended fitting 80 may provide greater accessibility to the reservoir 10 when the reservoir may need to be removed or replaced.

In some embodiments, the molded junction fitting 78 may include a recessed fitting 82. In some embodiments, the reservoir 10 may engage in an interference fit with an interior surface of the recessed fitting 82. In some embodiments, the recessed fitting 82 may minimize the projection of the reservoir 10 from an outer surface 70 of the catheter interface 60.

Figure 4C:
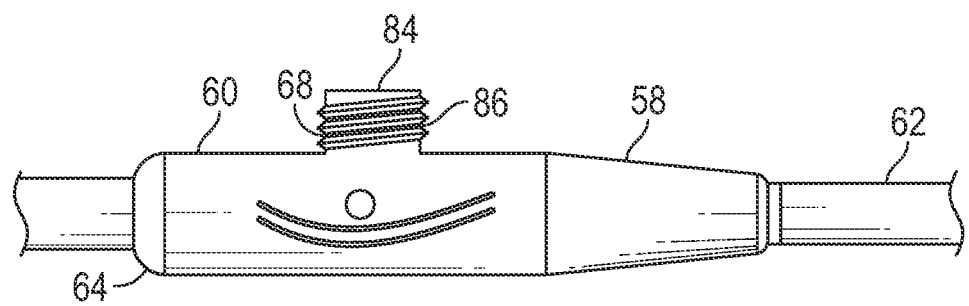
FIG. 4C is a side view of another example vascular access device, according to some embodiments.
Figure 4D:
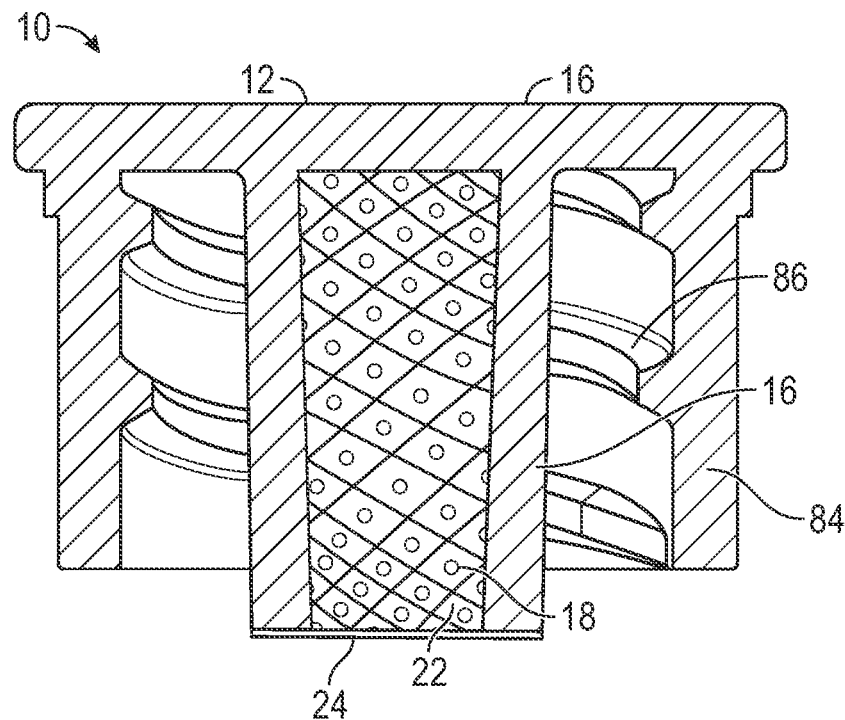
FIG. 4D is a cross-sectional view of another example reservoir, according to some embodiments.

Referring now to FIGS. 4C-4D, in some embodiments, the connector 68 may be a luer connector 84. In some embodiments, the connector 68 may include luer connector threads 86 that may couple to luer connector threads included on an outer surface of the impermeable gas wall 16 of the reservoir 10. In some embodiments, the connector 68 may include male or female luer threads 86. In some embodiments, the luer connector 84 of the reservoir may facilitate easy access or replacement of the reservoir when required.

Figure 4E:
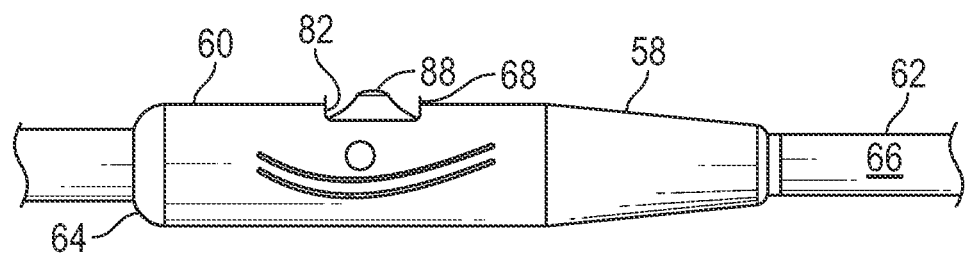
FIG. 4E is a side view of another example vascular access device, according to some embodiments.

Referring now to FIG. 4E, in some embodiments, the connector 68 may include a recessed projection 88. In some embodiments, the recessed projection 88 may extend from a recessed fitting 82 of the catheter interface 50. As described above, the opening 14 of the housing 12 of the reservoir 10 may include a seal 26. In some embodiments, upon coupling the reservoir 10 to the connector 68, the recessed projection 88 may pierce the seal 26, such that gaseous agent 20 may pass from the reservoir 10 through the connector 68 and into the one or more lumens 66. In some embodiments, the recessed projection 88 may include a fluid pathway 74 through the recessed projection.

Figure 5A:
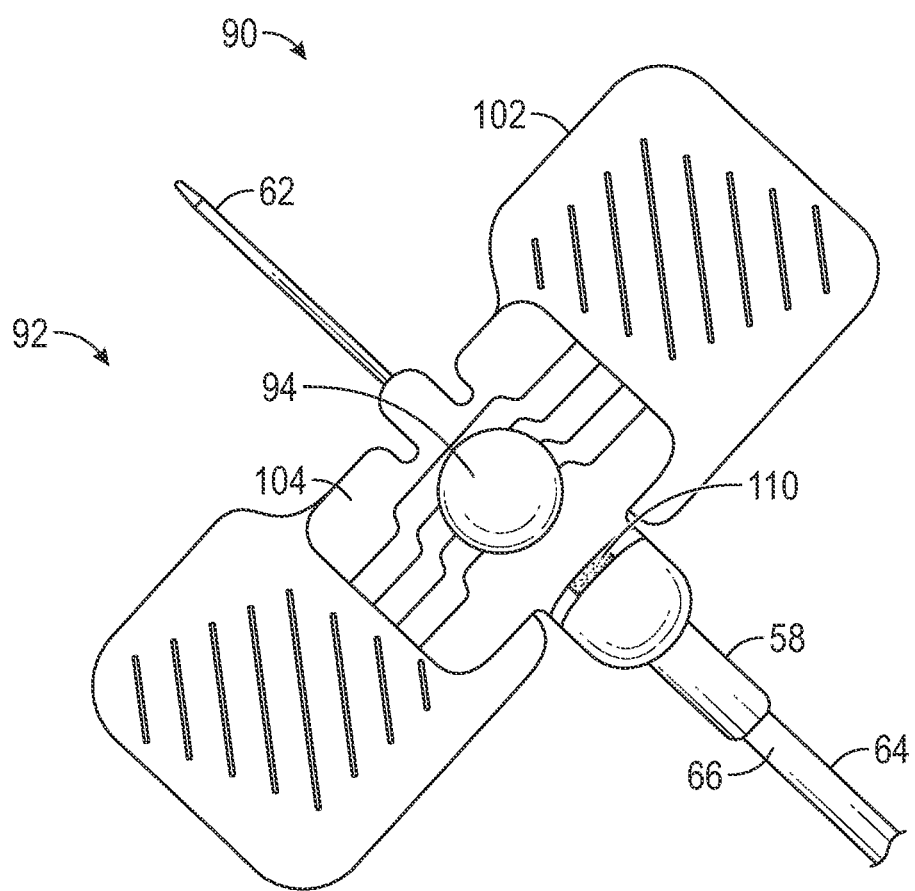
FIG. 5A is an upper perspective view of an example stabilization device, according to some embodiments.
Figure 5B:
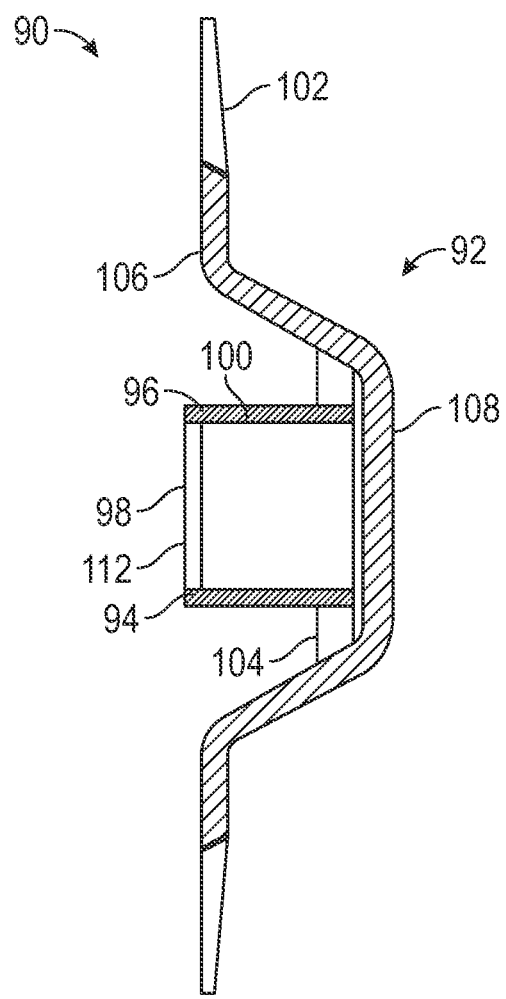
FIG. 5B is a cross-sectional view of the stabilization device of FIG. 6A, according to some embodiments.

Referring now to FIGS. 5A-5B, in some embodiments, a system 90 for infusing a gas into a vascular access device 58 may include a stabilization device 92. In some embodiments, the stabilization device 92 may be configured to couple to the vascular access device 58. In some embodiments, the system 90 may include a reservoir 94. In some embodiments, the reservoir 94 may include a housing 96 having an opening 98 and a gas impermeable wall 100. In some embodiments, the opening 98 may be configured to couple to the vascular access device 58 and the gas impermeable wall 100 may be configured to couple to the stabilization device 92. In some embodiments, the reservoir 94 may include the molecular precursor 18 to the gaseous agent 20. In some embodiments, the molecular precursor 18 may be suspended in the hydrogel 22 disposed within the housing 96. In some embodiments, the stabilization device 92 may be a StatLock® stabilization device, available from Becton, Dickinson & Company, and include the reservoir 94.

In some embodiments, the reservoir 94 may be similar or identical in terms of one or more included features and/or operation to one or more of the following: the reservoir 10 discussed with respect to FIGS. 1A-1B, 2A-2C, and 4A-4E.

In some embodiments, the stabilization device 92 may include an adhesive pad 102 and a retainer 104. In some embodiments, the retainer 104 may be coupled to the adhesive pad 102 and the adhesive pad 102 may be secured or anchored to an insertion site on the skin of the patient. In some embodiments, the adhesive pad 102 may be secured by an adhesive disposed upon the bottom surface of the adhesive pad 102. In some embodiments, the retainer 104 may be configured to receive the vascular access device 58 and secure it in position. In some embodiments, the retainer 104 may be configured to couple to the reservoir 94. In some embodiments, the retainer 104 may comprise several sub-components, including a base 106, a cover 108, and a latch 110 for coupling the retainer 104 to the vascular access device 58.

In some embodiments, the vascular access device 58 includes a connector 68 disposed on an outer surface 70. In some embodiments, the connector 68 includes a molded junction fitting 78, such that the opening 98 of the housing 96 may be coupled to the vascular access device 58 in an interference fit. In some embodiments, the reservoir 94 may be coupled to the stabilization device 92 in an interference fit. In some embodiments, the reservoir 94 may be removed from the stabilization device 92 and replaced. In other embodiments, the reservoir 94 may be coupled to the stabilization device 92 with an adhesive or glue.

In some embodiments, the base 106 of the retainer 104 couples the retainer 104 to the adhesive pad 102. In some embodiments, the cover 108 couples to the reservoir 94. In some embodiments, the cover 108 may be removed from the retainer 104 and replaced. Thus, the stabilization device 22 may be retained when the cover 108 is removed and replaced with another reservoir 94. In some embodiments, the latch 110 may couple with the vascular access device 58 in an interference fit. In some embodiments, the reservoir 94 may serve as the latch 110 because the reservoir 94 may couple with the vascular access device 58 in an interference fit.

In some embodiments, the opening 98 may include a membrane 112. In some embodiments, the membrane 112 may be similar or identical in terms of one or more included features and/or operation to one or more of the following: the membrane 24 discussed with respect to FIGS. 1A-1B, 2C, and 3A-3B.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A system for infusing a gas into a vascular access device, comprising:
    a catheter interface, wherein the catheter interface comprises a distal end, a proximal end, and one or more lumens extending between the distal end and the proximal end; and
    a connector disposed on an outer surface of the catheter interface, wherein the connector is configured to couple to a reservoir and allow passage of a gaseous agent from the reservoir to the one or more lumens, wherein the reservoir comprises:
        a housing comprising an opening and an impermeable wall, wherein the opening is configured to couple to the connector of the catheter interface; and
        a molecular precursor to the gaseous agent suspended in a hydrogel disposed within the housing, wherein the gaseous agent is antimicrobial, antithrombogenic, or both antimicrobial and antithrombogenic.

2. The system of claim 1, wherein the gaseous agent permeates through the connector and into the one or more lumens, wherein the gaseous agent provides antimicrobial, antithrombogenic, or both antimicrobial and antithrombogenic protection to at least one surface of the system.

3. The system of claim 1, further comprising a fluid pathway in fluid communication between the reservoir and the one or more lumens.

4. The system of claim 1, wherein the connector is a luer connector or a molded junction fitting such that the housing mechanically couples to the catheter interface in an interference fit.

5. The system of claim 1, wherein the connector further comprises a recessed projection and the opening of the housing further comprises a seal, wherein upon coupling the connector to the reservoir the recessed projection pierces the seal.

6. The system of claim 1, wherein the connector further comprises a membrane, wherein the membrane is gas-permeable and hydrophobic.

7. The system of claim 1, wherein the opening of the housing further comprises a membrane, wherein the membrane is gas-permeable and hydrophobic.

8. The system of claim 1, wherein the gaseous agent is nitric oxide and wherein the molecular precursor to the gaseous agent is selected from S-nitroso-N-acetylpenicillamine, S-nitrosoglutathione, sodium nitroprusside, or a combination thereof.

* * * * *